United States Patent
Huang et al.

(10) Patent No.: US 12,048,503 B2
(45) Date of Patent: Jul. 30, 2024

(54) MEDICAL DEVICE FOR MANIPULATING SURGICAL TOOL

(71) Applicant: Point Robotics Medtech Inc., Hsinchu County (TW)

(72) Inventors: Kun-Pin Huang, Hsinchu County (TW); Chih-Hsiang Hsieh, Hsinchu County (TW); Chao-Wei Wu, Hsinchu County (TW); Ming-Chun Ho, Hsinchu County (TW)

(73) Assignee: POINT ROBOTICS (SINGAPORE) PTE. LTD., Singapore (SG)

( * ) Notice: Subject to any disclaimer, the term of this patent is extended or adjusted under 35 U.S.C. 154(b) by 107 days.

(21) Appl. No.: 18/069,230

(22) Filed: Dec. 21, 2022

(65) Prior Publication Data

US 2023/0118765 A1    Apr. 20, 2023

Related U.S. Application Data

(63) Continuation-in-part of application No. 17/138,805, filed on Dec. 30, 2020, now Pat. No. 11,696,809.

(30) Foreign Application Priority Data

Mar. 28, 2022 (TW) .................................. 111111535

(51) Int. Cl.
| | |
|---|---|
| *A61B 90/00* | (2016.01) |
| *A61B 34/00* | (2016.01) |
| *A61B 17/00* | (2006.01) |
| *A61B 90/50* | (2016.01) |

(52) U.S. Cl.
CPC ...... *A61B 34/70* (2016.02); *A61B 2017/0069* (2013.01); *A61B 2017/0084* (2013.01); *A61B 2090/064* (2016.02); *A61B 2090/506* (2016.02); *A61B 2562/0252* (2013.01)

(58) Field of Classification Search
CPC . B25J 9/1623; B25J 13/085; A61B 2090/064; A61B 2090/065; A61B 34/70; A61B 90/06
See application file for complete search history.

(56) References Cited

U.S. PATENT DOCUMENTS

| | | | | |
|---|---|---|---|---|
| 9,561,082 | B2* | 2/2017 | Yen | A61B 34/30 |
| 11,324,557 | B2* | 5/2022 | Shelton, IV | H03K 17/962 |
| 2009/0301253 | A1* | 12/2009 | Nishida | G05B 15/02 |
| | | | | 901/20 |
| 2012/0143084 | A1* | 6/2012 | Shoham | B25J 9/1676 |
| | | | | 901/41 |
| 2013/0096574 | A1* | 4/2013 | Kang | A61B 17/1622 |
| | | | | 606/130 |
| 2020/0008889 | A1* | 1/2020 | Ho | A61B 17/34 |

* cited by examiner

*Primary Examiner* — Randell J Krug
(74) *Attorney, Agent, or Firm* — Li & Cai Intellectual Property Office

(57) ABSTRACT

A medical device is provided. The medical device includes a parallel manipulator. The parallel manipulator has an end platform coupled to a surgical tool and a base platform coupled to a machine module. The machine module is coupled to the surgical tool through a transmission shaft disposed between the end platform and the base platform. The transmission shaft has a transmission yoke, a runner, a first rod coupled to the transmission yoke, a second rod coupled to the runner, and a universal joint coupled between the first rod and the second rod.

16 Claims, 12 Drawing Sheets

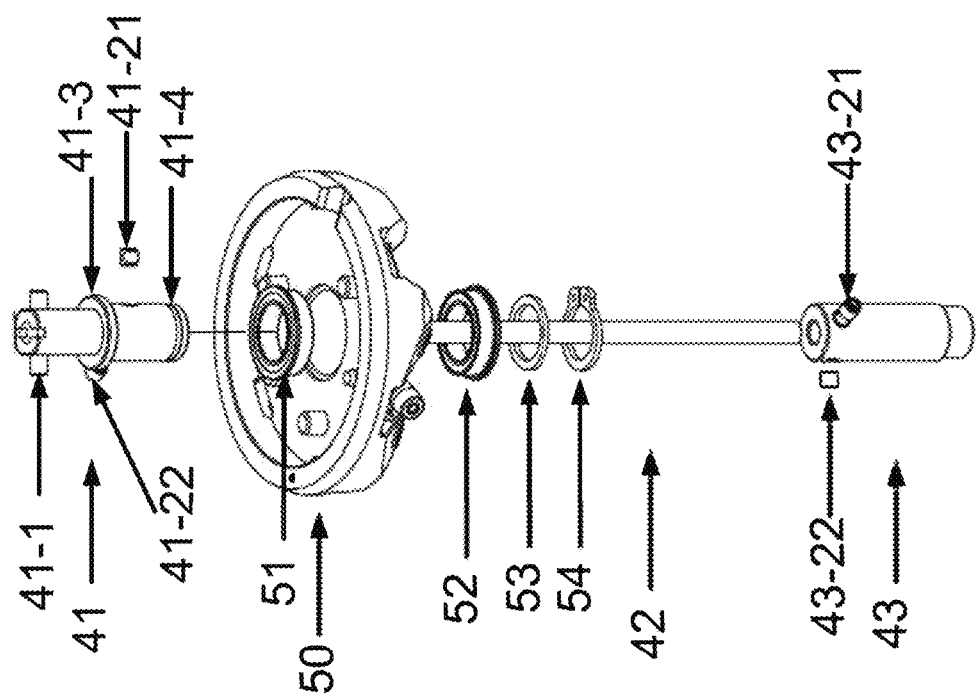

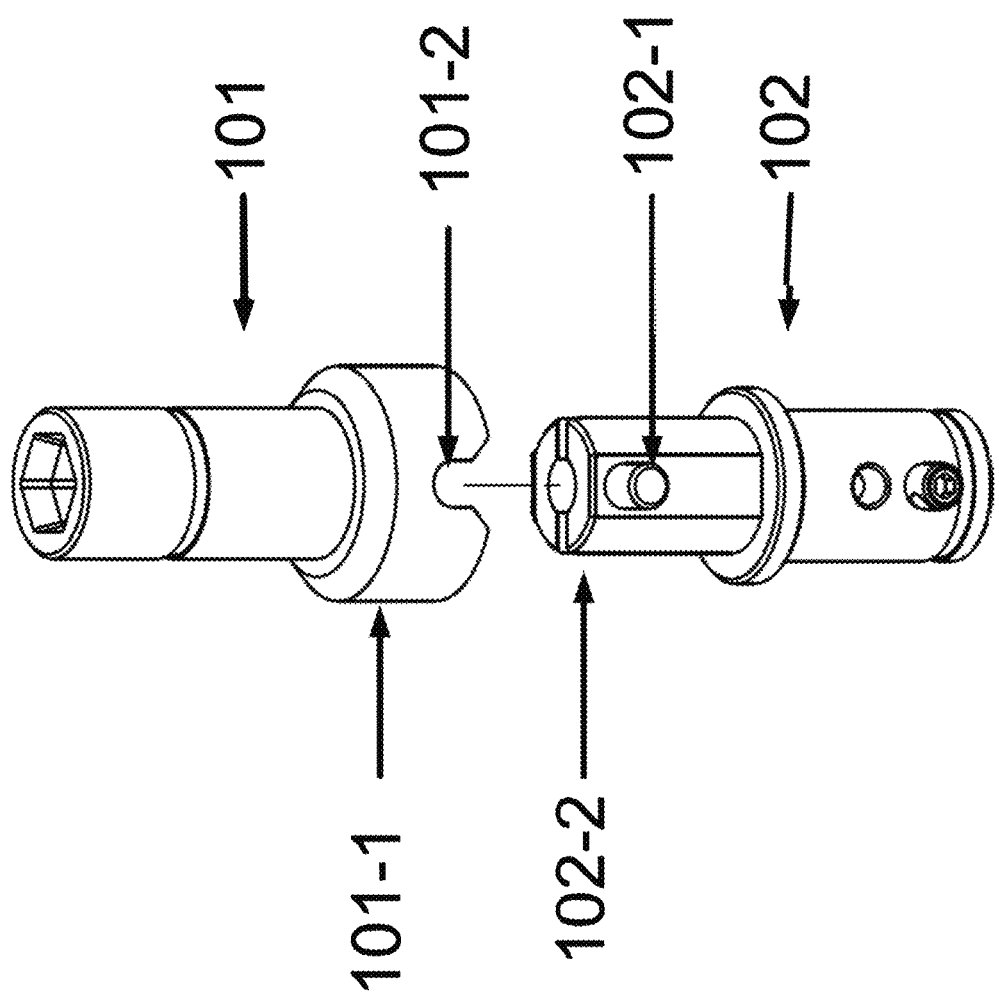

MEDICAL DEVICE FOR MANIPULATING SURGICAL TOOL

CROSS-REFERENCE TO RELATED PATENT APPLICATION

This application is a continuation-in-part of U.S. application Ser. No. 17/138,805, filed on Dec. 30, 2020 and entitled "MEDICAL DEVICE FOR MANIPULATING SURGICAL TOOLS", the contents of which are incorporated herein by reference in their entireties.

This application also claims the benefit of priority to Taiwan Patent Application No. 111111535, filed on Mar. 28, 2022. The entire content of the above identified application is incorporated herein by reference.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure generally relates to a medical device, and more particularly to a medical device having a transmission shaft between an end platform and a base platform of a parallel manipulator and configured to transfer mechanical force.

BACKGROUND OF THE DISCLOSURE

A parallel mechanism is capable of positioning and orienting an end platform with up to six or more degrees of freedom. The end platform of a parallel mechanism can be used to support a medical device, such as a diagnostic device or a surgical instrument. Since the end platform parallel mechanism can be made extremely small, the mechanism can be used either for surgery through a large surgical opening or for endosurgery through a small surgical opening or body orifice.

Because the end platform is capable of being manipulated with high accuracy and agility, the parallel mechanism is particularly suitable for use in surgery by remote control. The ability of the mechanism to adjust the position of the end platform makes the mechanism suitable for medical applications that require precision and fine motions. However, having a motor for controlling the surgical instrument mounted at the end platform can cause additional weight and force to be applied to the end platform during operation. The additional weight and force may affect the response time and the precision of the range/path of the planned operation. Therefore, in order to increase the precision of the medical device, there is a need to minimize the force exerted upon the end platform of the parallel manipulator.

SUMMARY OF THE DISCLOSURE

In response to the above-referenced technical inadequacies, the present disclosure provides a medical device with a transmission shaft.

In one aspect, the present disclosure provides a medical device, including: a parallel manipulator, an adapter, a transmission shaft and a shaft motor. The parallel manipulator includes an end platform and a base platform mechanically coupled to the end platform. The adapter includes a body detachably coupled to the end platform and a receiving shaft rotatably supported by the body, and the receiving shaft having a receiving yoke. The transmission shaft is rotatably supported by the end platform, and the transmission shaft includes a transmission yoke configured to transfer mechanical force to the receiving yoke, a first rod coupled to the transmission yoke, a second rod coupled to the first rod, a universal joint coupled between the first rod and the second rod, and a runner coupled to the second rod. The shaft motor is configured to generate mechanical force to drive the transmission shaft, and the shaft motor has a drive shaft slidably engaged to the runner.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The described embodiments may be better understood by reference to the following description and the accompanying drawings, in which:

FIG. 5 illustrates an exploded view of a transmission shaft according to some embodiments of the instant disclosure;

FIG. 10 illustrates a perspective view of a receiving shaft and a transmission yoke according to some embodiments of the instant disclosure;

DETAILED DESCRIPTION OF THE EXEMPLARY EMBODIMENTS

Figure 1:
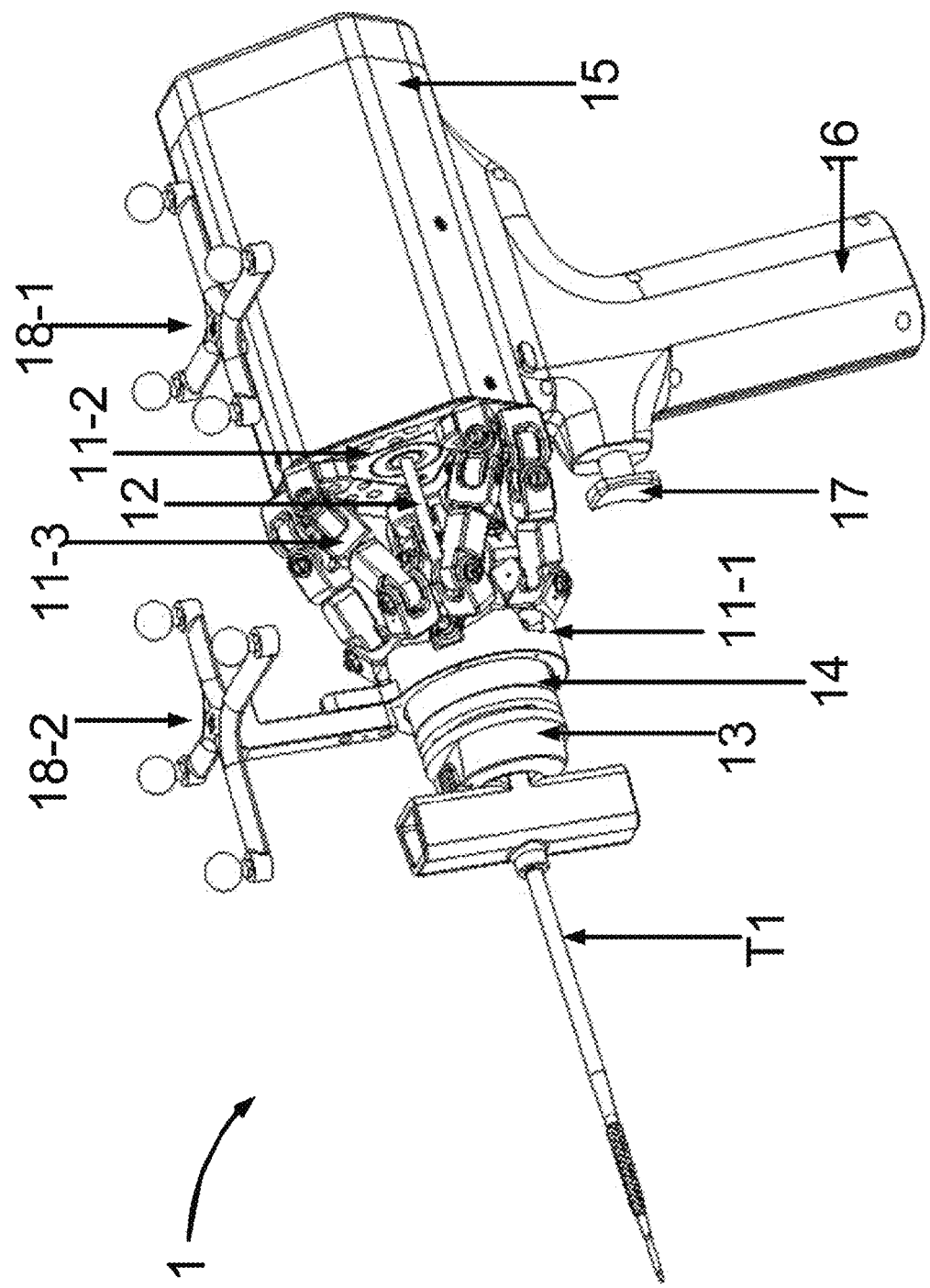
FIG. 1 illustrates a three-dimensional view of a medical device according to some embodiments of the instant disclosure.

The present disclosure will now be described more fully hereinafter with reference to the accompanying drawings, in which exemplary embodiments of the disclosure are shown.

This disclosure may, however, be embodied in many different forms and should not be construed as limited to the exemplary embodiments set forth herein. Rather, these exemplary embodiments are provided so that this disclosure will be thorough and complete, and will fully convey the scope of the disclosure to those skilled in the art. Like reference numerals refer to like elements throughout.

The terminology used herein is for the purpose of describing particular exemplary embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," or "includes" and/or "including" or "has" and/or "having" when used herein, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments will be described below with reference to the accompanying drawings. It should be noted that elements depicted in the reference figures are not necessarily shown to scale; rather, the same or similar components will be given the same or similar reference numerals or similar technical terms.

Figure 2:
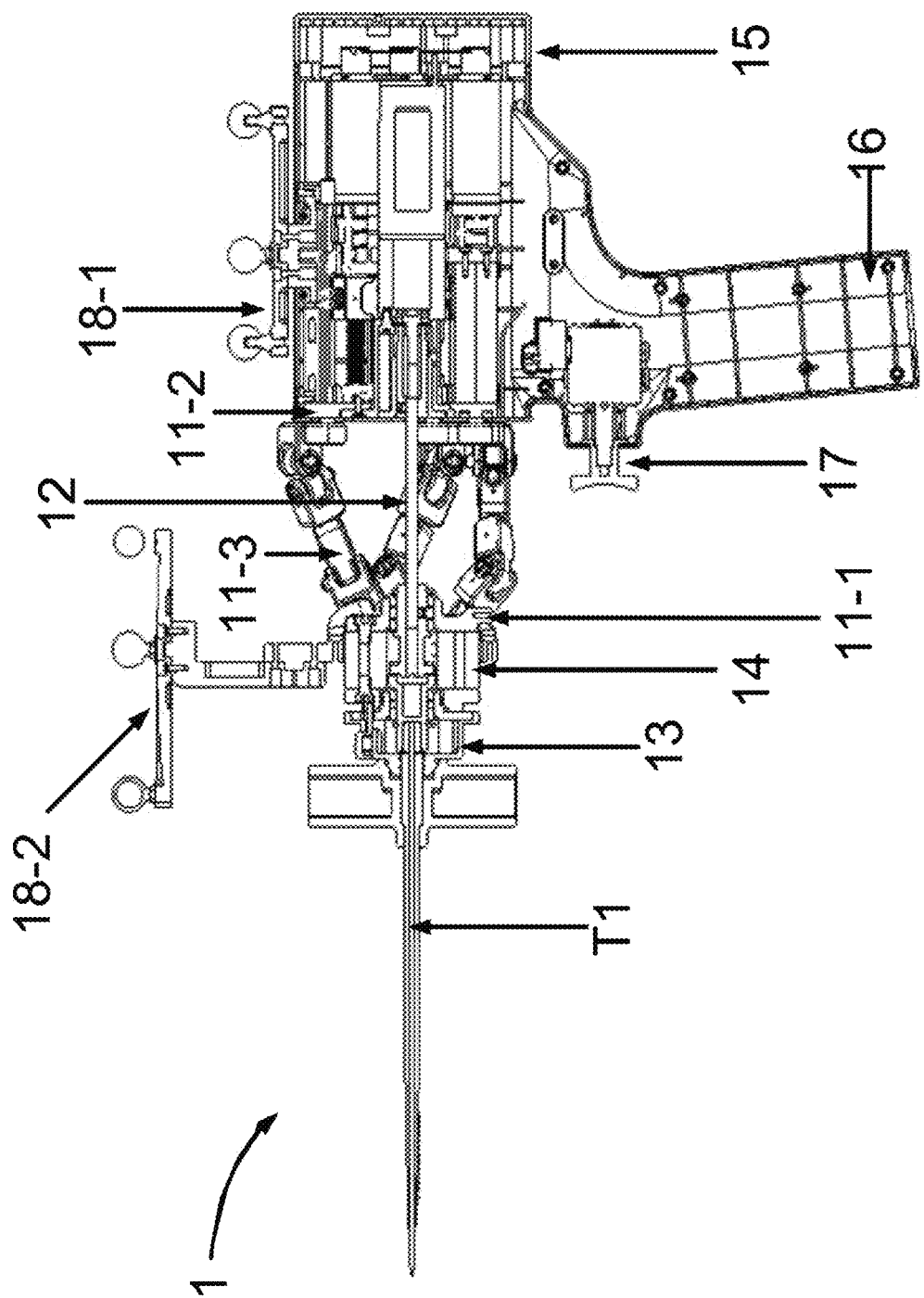
FIG. 2 illustrates a cross-sectional view of a medical device according to some embodiments of the instant disclosure.
Figure 3:
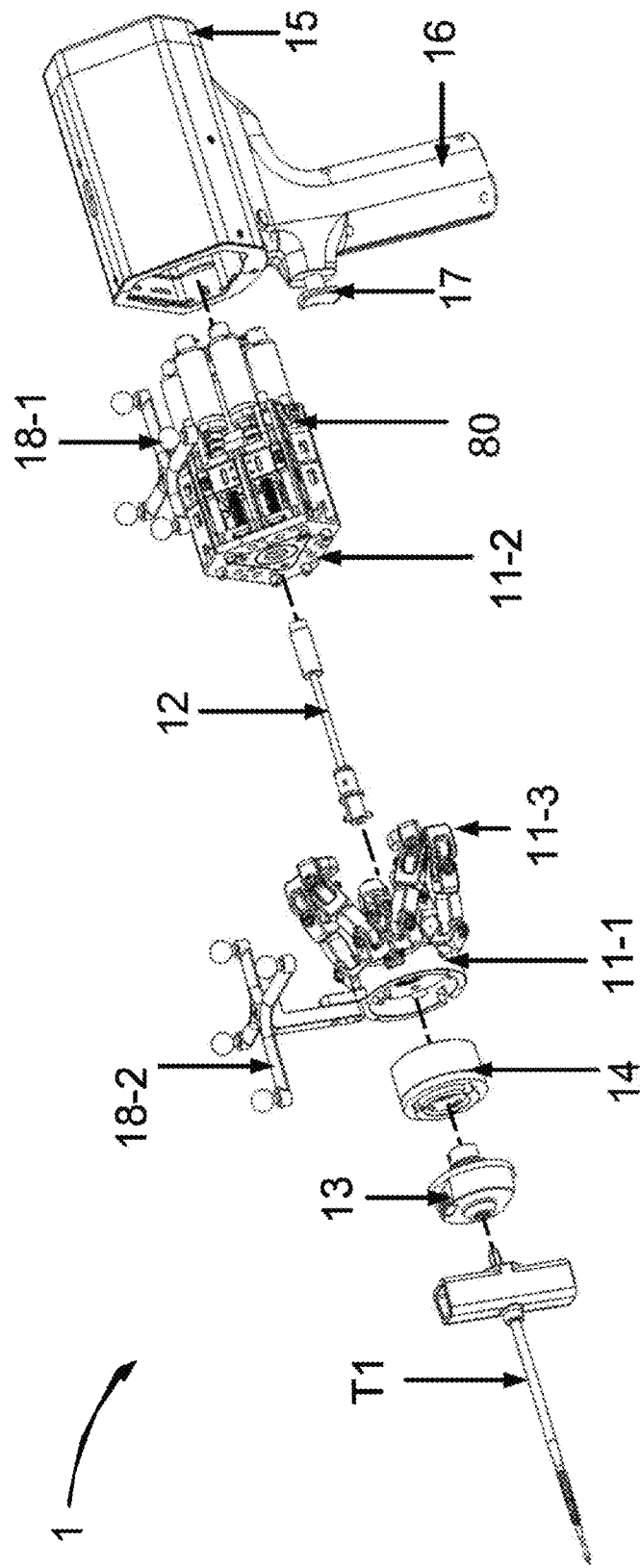
FIG. 3 illustrates an exploded view of a medical device according to some embodiments of the instant disclosure.

FIG. 1 illustrates a three-dimensional view of a medical device according to some embodiments of the instant disclosure. FIG. 2 illustrates a cross-sectional view of a medical device according to some embodiments of the instant disclosure. FIG. 3 illustrates an exploded view of a medical device according to some embodiments of the instant disclosure. In some embodiments, the medical device 1 includes a parallel manipulator, a transmission shaft 12, and an adapter 13. The parallel manipulator includes an end platform 11-1, a base platform 11-2, and a plurality of limbs 11-3 operably coupled between the end platform 11-1 and the base platform 11-2. The transmission shaft 12 is disposed between the end platform 11-1 and the base platform 11-2. Further, the transmission shaft 12 is rotatably supported by the end platform 11-1. In some embodiments, the adapter 13 is configured to hold a surgical tool T1, such as a drill bit, a trocar, or a saw blade. In some embodiments, the medical device 1 further includes a sensor system 14 disposed between the adapter 13 and the end platform 11-1. The sensor system 14 is configured to monitor the force exerted and received by the adapter 13.

In some embodiments, the medical device 1 further includes a housing 15, a handle 16, and a control module 17. The base platform 11-2 is mechanically attached to the housing 15 and accommodates a machine module 19 configured to manipulate the movement of the plurality of limbs 11-3, which in turn control the movement of the end platform 11-1. The machine module 19 includes a plurality of actuators for correspondingly manipulating the plurality of limbs 11-3 and a shaft motor for manipulating the transmission shaft 11-2. The handle 16 allows user to hold onto and maneuver the medical device 1 during operation. The control module 17 allows the user to trigger, halt, or adjust actions of the surgical tool T1 or perform other functions of the medical device 1.

Parallel manipulators may be classified based on degree of freedom, number of limbs, order of joints in each limb, and type of actuator. In some embodiments, the parallel manipulator can be a hexa-axes parallel manipulator with six degrees of freedom (6-DOF). In some embodiments, the plurality of limbs 11-3 comprises six limbs. In some embodiments, each limb 11-3 has a first joint coupled to an actuator underneath the base platform 11-2, a second joint coupled to the end platform 11-1, and a third joint between the first joint and the second joint. In some embodiments, the parallel manipulator is a 6-PUS parallel manipulator. In some embodiments, the first joint is a prismatic joint. In some embodiments, the second joint is a spherical joint. In some embodiments, the third joint is a universal joint. The universal joint is formed using two revolute joints.

In some embodiments, the medical device 1 further includes a first positioning unit 18-1 and a second positioning unit 18-2. The first positioning unit 18-1 and the second positioning unit 18-2 correspondingly include a plurality of markers for emitting electromagnetic signals, sound wave, heat, or other perceivable signals, and adapters for mounting the markers at particular orientations with respect to the body of the device. In some embodiments, the markers and adapters are used in cooperation with a spatial sensor for object tracking functionalities during operation. The second positioning unit 18-2 may be disposed in an area between the adapter 13 and the end platform 11-1. In some embodiments, the second positioning unit 18-2 is disposed on the end platform 11-1. In some other embodiments, the second positioning unit 18-2 is disposed on the adapter 13. In some other embodiments, the second positioning unit 18-2 is disposed on the tool T1.

Figure 4A:
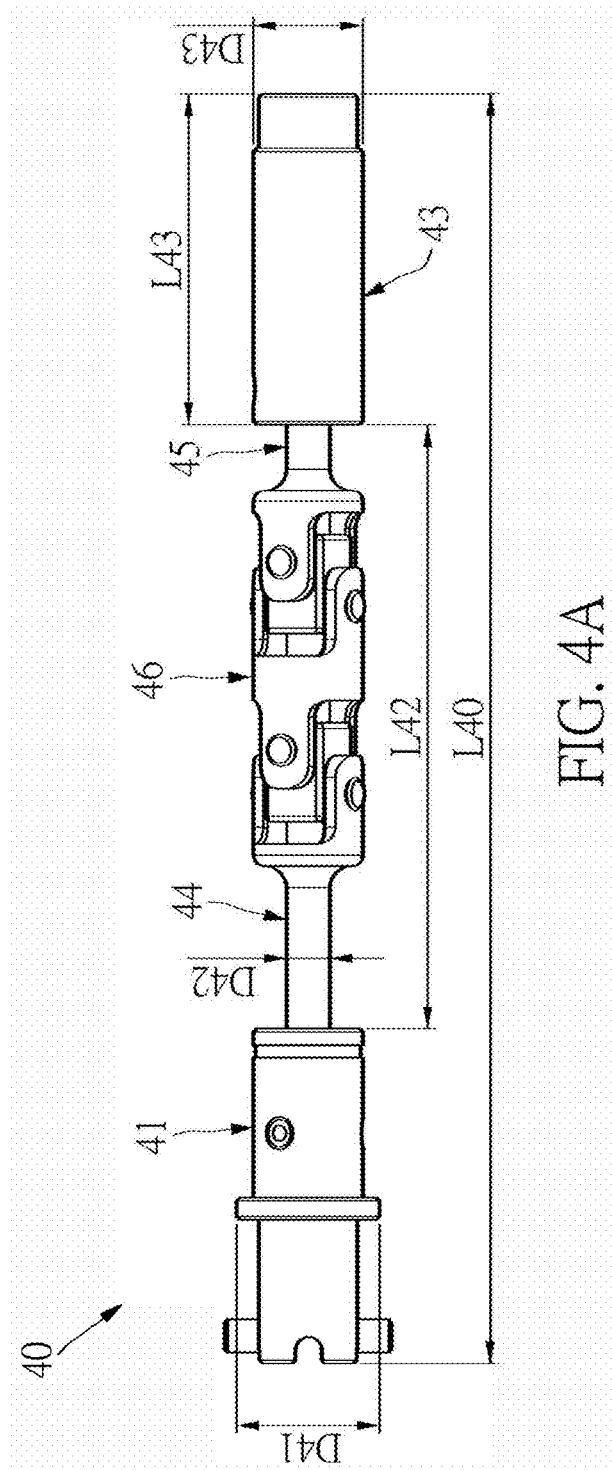
FIG. 4A illustrates a perspective view of a transmission shaft according to some embodiments of the instant disclosure.
Figure 4B:
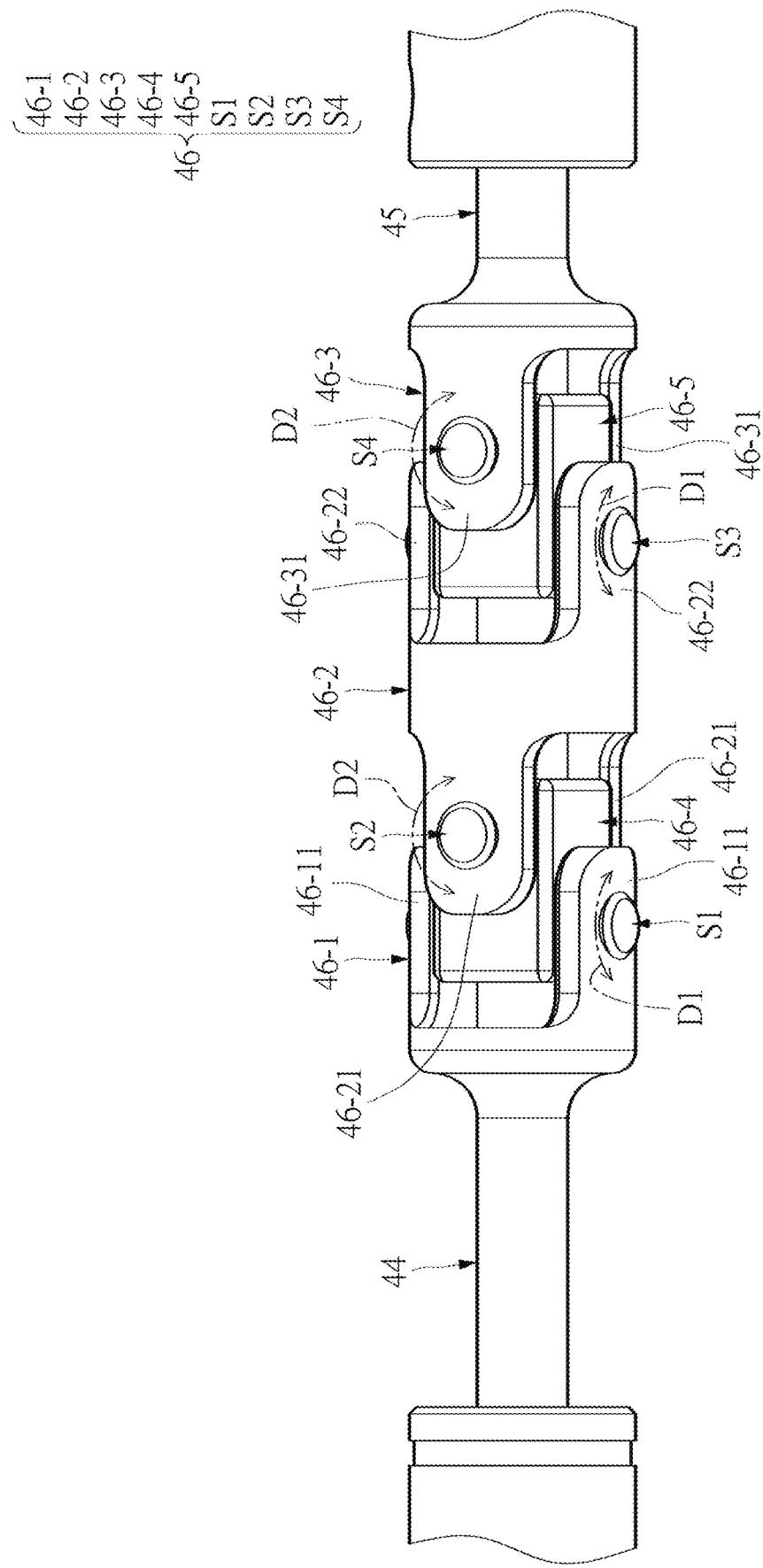
FIG. 4B illustrates a schematic view of a universal joint according to some embodiments of the instant disclosure.

FIG. 4A illustrates a perspective view of a transmission shaft according to some embodiments of the instant disclosure. FIG. 4B illustrates a schematic view of a universal joint according to some embodiments of the instant disclosure. In some embodiments, the transmission shaft 40 is rotatably supported by the end platform and slidingly engaged to the base platform. In some embodiments, the transmission shaft 40 includes a transmission yoke 41 configured to transfer a mechanical force to a surgical tool (i.e., surgical tool T1 in FIG. 1), a first rod 44 coupled to the transmission yoke 41, a second rod 45 coupled to the first rod 44, and a universal joint 46 coupled between the first rod 44 and the second rod 45. In some embodiments, the universal joint 46 (including connecting shafts in the universal joint) is made of solid metal with better structural strength, such that the universal joint 46 has a longer service life than that of a pliable rod made of a metal spring tube. The universal joint 46 structurally adapts to the applied force and returns to its original structure when force is removed. The universal joint 46 is stiff enough to endure and transfer the mechanical force from the shaft motor. In one exemplary embodiment, the universal joint 46 includes a first coupler 46-1 coupled to the first rod 44, a second coupler 46-2 coupled to the first coupler 46-1, and a third coupler 46-3 coupled between the first coupler 46-1 and the second rod 45. As shown in FIG. 4B, the first coupler 46-1 is pivotably coupled with the second coupler 46-2 through a first connecting shaft S1 and a second connecting shaft S2, and the first coupler 46-1 is swingable with respect to the second coupler 46-2 along a first direction D1 and a second direction D2. In addition, the second coupler 46-2 is pivotably coupled with the third coupler 46-3 through a third connecting shaft S3 and a fourth connecting shaft S4, and the second coupler 46-2 is swingable with respect to the third coupler 46-3 along the first direction D1 and the second direction D2. Specifically, the first coupler 46-1 rotates in the first direction D1 relative to the second coupler 46-2 with the first connecting shaft S1 as one center, and rotates in the second direction D2 relative to the second coupler 46-2 with the second connecting shaft S2 as another center. In addition, the second coupler 46-2 rotates in the first direction D1 relative to the third coupler 46-3 with the third connecting shaft S3 as one center, and rotates in the second direction D2 relative to the third coupler 46-3 with the fourth connecting shaft S4 as another center. Since the transmission shaft 40 is rotatable, neither the first direction D1 nor the second direction D2 is a fixed direction, as long as planes corresponding to the first direction D1 and the second direction D2 are perpendicular to one another.

In some embodiments, the universal joint 46 can further include a fourth coupler 46-4 coupled between the first coupler 46-1 and the second coupler 46-2, and a fifth coupler 46-5 coupled between the second coupler 46-2 and the third coupler 46-3. As shown in FIG. 4B, the first coupler 46-1 is pivotably coupled to the fourth coupler 46-4 about the first connecting shaft S1, and the second coupler 46-2 is pivotably coupled to the fourth coupler 46-4 about the second connecting shaft S2. In addition, the second coupler 46-2 is pivotably coupled to the fifth coupler 46-5 about the third connecting shaft S3, and the third coupler 46-3 is pivotably coupled to the fifth coupler 46-5 about the fourth connecting shaft S4. In some embodiments, the fourth coupler 46-4 has a first through hole and a second through hole, and one end of the first coupler 46-1, adjacent to the fourth coupler 46-4, has a pair of first pivot ears 46-11. The first connecting shaft S1 penetrates the pair of first pivot ears 46-11 and the first through hole, such that the first coupler 46-1 is pivotally coupled to the fourth coupler 46-4 about the first connecting shaft S1. In addition, one end of the second coupler 46-2, adjacent to the fourth coupler 46-4, has a pair of second pivot ears 46-21. The second connecting shaft S2 penetrates the pair of second pivot ears 46-21 and the second through hole, such that the second coupler 46-2 is pivotally coupled to the fourth coupler 46-4 about the second connecting shaft S2. Correspondingly, the fifth coupler 46-5 has a third through hole and a fourth through hole, and one end of the second coupler 46-2, adjacent to the fifth coupler 46-5, has a pair of third pivot ears 46-22. The third connecting shaft S3 penetrate through the pair of third pivot ears 46-22 and the third through hole, such that the second coupler 46-2 can be pivotally coupled to the fifth coupler 46-5 about the third connecting shaft S3. In addition, a pair of fourth pivot ears 46-31 is disposed at one end of the third coupler 46-3 and adjacent to the fifth coupler 46-5, and the fourth shaft S4 penetrates the pair of fourth pivot ears 46-31 and the fourth through hole, such that the third coupler 46-3 is pivotally coupled to the fifth coupler 46-5 about the fourth connecting shaft S4. In some embodiments, each of two ends of the universal joint 46 has a structure with a stop screw locked and fastened to a milling plane of a solid metal shaft. Therefore, the defect of an insufficient tightening force due to structural deformation will not occur to the milling plane under long-term use. In some embodiments, a maximum distance between the end platform and the base platform is greater than a sum of lengths of the first rod 44, the universal joint 46 and the second rod 45, and a minimum distance between the end platform and the base platform is substantially the same as the sum of lengths of the first rod 44, the universal joint 46 and the second rod 45. In this way, the universal joint 46 will not be compressed when the medical device is not in use.

In some embodiments, during operation of the medical device, only the first rod 44, the universal joint 46 and the second rod 45 are exposed between the end platform and the base platform when the end platform and the base platform are at the minimum distance from each other. In some other embodiments, during operation of the medical device, the first rod 44, the universal joint 46, the second rod 45, and a portion of the runner are exposed between the end platform and the base platform when the end platform and the base platform are at the minimum distance from each other. In other words, the runner is substantially coplanar with the base platform when the end platform and the base platform are at the minimum distance from each other.

On the other hand, a portion of the runner is exposed between the end platform and the base platform when the distance between the end platform and the base platform are greater than the minimum distance. When the end platform and the base platform are at the maximum distance from each other, an overlap between the runner and the drive shaft is no less than 5 mm. However, in some other embodiments, an overlap between the runner and the drive shaft may be less than 5 mm when the distance between the end platform and the base platform is at the maximum. In other words, a minimum overlap between the runner and the drive shaft is no less than 5 mm During operation, a force may be applied to the universal joint 46 which causes the first coupler 46-1 and the second coupler 46-2 to swing, and in response to removing of the applied force, the first coupler 46-1 and the second coupler 46-2 return to their original states.

In some embodiments, the runner is substantially coplanar with the base platform when the end platform and the base platform are at the minimum distance from each other. Further, the sum of lengths of the first rod 44, the universal joint 46 and the second rod 45 is substantially the same as the minimum distance between the end platform and the base platform. In other embodiments, the runner protrudes from the base platform when the end platform and the base platform are at the minimum distance from each other. Further, the sum of lengths of the first rod 44, the universal joint 46 and the second rod 45 is less than the minimum distance between the end platform and the base platform. In some other embodiments, the runner is recessed from the base platform when the end platform and the base platform are at the minimum distance from each other. Further, the sum of lengths of the first rod 44, the universal joint 46 and the second rod 45 is greater than the minimum distance between the end platform and the base platform. However, while the distance between the end platform and the base platform is at the minimum, the universal joint 46 is at a normal state. In some embodiments, the normal state of the universal joint 46 is a state in which the pliable rod experiences relatively no force no force is applied on the universal joint 46, as compared to the swinging state of the universal joint 46. Thus, the universal joint 46 maintains its original shape (i.e., the first coupler 46-1 and the second coupler 46-2 do not swing) during the normal state.

In an exemplary embodiment, a length L40 of the transmission shaft 40 is substantially 11.5 cm (i.e., 11.495 cm). In an exemplary embodiment, the combined length L42 of the first rod 44, the universal joint 46 and the second rod 45 is substantially 5.5 cm (i.e., 5.475 cm). In an exemplary embodiment, diameters D42 of the first rod 44 and the second rod 45 are substantially 0.38 cm. In an exemplary embodiment, a diameter D43 of the runner 43 is substantially 1 cm. In an exemplary embodiment, a length L43 of the runner 43 is substantially 3 cm (i.e., 2.995 cm). In an exemplary embodiment, a diameter D41 of a widened part of the transmission yoke 41 is substantially 1.3 cm. However, the above-mentioned dimensions are only examples, and should not be used to limit the scope of the disclosure.

FIG. 5 illustrates an exploded view of a transmission shaft according to some embodiments of the instant disclosure. In some embodiments, the first rod 44, the universal joint 46 and the second rod 45 can be collectively referred to as a universal joint drive shaft 42, and for the convenience of the following description, the universal joint drive shaft 42 is simplified as a rod in FIG. 5. The transmission yoke 41 and the runner 43 correspondingly have a through hole into which the universal joint drive shaft 42 is inserted. To physically attach the universal joint drive shaft 42 to the transmission yoke 41 and the runner 43, pins 41-21, 41-22, 43-21, and 43-22 are correspondingly used. The pins 41-21 and 41-22 are used to pin or press one end of the universal joint drive shaft 42 to an inner surface of the through hole of the transmission yoke 41. In some embodiments, the pins 41-21 and 41-22 are disposed orthogonally to each other. The pins 43-21 and 43-22 are used to pin or press another end of the universal joint drive shaft 42 to an inner surface of the through hole of the runner 43. In some embodiments, the pins 43-21 and 43-22 are disposed orthogonally to each other. Therefore, orthogonal positioning of the pins 41-21, 41-22, 43-21, and 43-22 ensure that the universal joint drive shaft 42 is securely fastened to the transmission yoke 41 and the runner 43 during operation.

In a case of using a pliable rod which is composed of a metal spring tube and coupled between the transmission yoke 41 and the runner 43, lifetime is relatively low due to fatigue of the metal spring. Therefore, the pliable rod may be composed of multiple bundles of thin metal wires wrapped with a spring wire. In addition, the pliable rod must be maintained at a bending state as it is in use, the rigidity of the pliable rod cannot be too stiff. However, a diameter of the spring wire of the pliable rod affects the rigidity. To make the pliable rod have elasticity and bendability, it is necessary to use the spring wire with a smaller diameter; however, such spring wire does not last long. In addition, the transmission shaft 12 can transmit a rotational torque from the shaft motor to the surgical tool T1. However, metal dust may be generated due to friction between metal surfaces of the spring wire while the pliable rod rotates, thus increasing the risk of damaging the inside of the platform. Therefore, in the medical device 1 provided by the present disclosure, the universal joint 46 can be utilized to connect the transmission yoke 41 and the sliding member 43, and the universal joint 46 can cooperate with the end platform to perform multi-directional movement. The motion capability of six degrees of freedom can be achieved, and the issue of poor lifetime of the pliable rod composed of the metal spring tube can be resolved as well. In addition, dust is less likely to be generated by friction as the universal joint 46 rotates, thereby reducing the risk of damage to the interior of the platform.

In some embodiments, the transmission yoke 41 includes a protrusion 41-1 configured to transfer a mechanical force to a receiving shaft of the adapter (i.e., adapter 13 in FIG. 1). The protrusion 41-1 is configured to have minimal contact to the receiving shaft of the adapter during operation to prevent noise (meaningless or unwanted mechanical force input) on the adapter.

As shown in FIG. 5, the end platform 50 includes a first bearing 51 and a second bearing 52. In some embodiments, the end platform 50 further includes a washer 53 and a retaining ring 54. In some embodiments, the first bearing 51 and the second bearing 52 are flanged bearings in which an extension or a lip on an outer ring of the bearing is designed to aid the mounting and positioning of the bearing. In some embodiments, a flange of the first bearing 51 is positioned on a surface of the end platform 50 facing away from the base platform (i.e., positioning between the end platform 11-1 and the adapter 13 in FIG. 3). In some embodiments, a flange of the second bearing 52 is positioned on a surface of the end platform 50 facing towards the base platform (i.e., positioning between the end platform 11-1 and the base platform 11-2 in FIG. 3).

In some embodiments, the retaining ring 54 is radially installed on a groove 41-4 of the transmission yoke 41. The retaining ring 54 may be a C-ring. In some embodiments, the washer 53 is disposed between retaining ring 54 and the second bearing 52 to prevent abrasion of the second bearing 52. Further, the washer 53 is used to fill the gap between the flange 41-3 of the transmission yoke 41 and retaining ring 54. In some embodiments, the gap between the flange 41-3, the end platform 50, the washer 53, the first bearing 51, and the second bearing 52 is substantially removed through the use of the retaining ring 54. The bearings 51 and 52 may be sandwiched between the flange 41-3 of the transmission yoke 41 and the retaining ring 54. Thus, the flange 41-3 of the transmission yoke 41 and the retaining ring 54 are used to aid the mounting and positioning of the transmission yoke 41.

Figure 6:
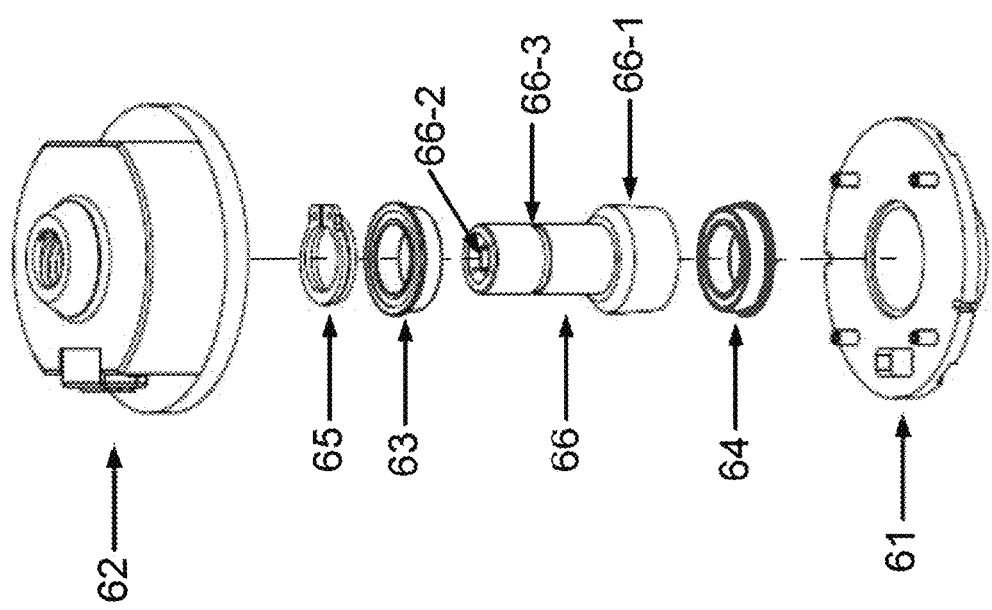
FIG. 6 illustrates an exploded view of an adapter according to some embodiments of the instant disclosure.

FIG. 6 illustrates an exploded view of an adapter according to some embodiments of the instant disclosure. In some embodiments, the adapter includes a body and a receiving shaft 66 disposed within and rotatably supported by the body. The body includes a base 61 and a cover 62 mechanically attached to the base 61. The receiving shaft 66 is disposed between the base 61 and the cover 62. In some embodiments, the receiving shaft 66 includes a receiving yoke 66-1 and a chuck 66-2 opposite the receiving yoke 66-1. The chuck 66-2 is configured to hold a surgical tool (i.e., surgical tool T1 in FIG. 1). The chuck 66-2 is aligned with a through hole of the cover 62 where a surgical tool may be inserted. The receiving yoke 66-1 is exposed outside of the adapter. In this way, receiving yoke 66-1 can receive mechanical force from the transmission shaft. The contact between the receiving yoke 66-1 and the transmission shaft is designed to be as minimal as possible to prevent generation of noise. In some embodiments, a groove (not shown) is formed on the receiving yoke 66-1 complementary to a protrusion (i.e., protrusion 41-1 in FIG. 5) of the transmission shaft for receiving the mechanical force.

In some embodiments, the adapter further includes a first bearing 63 and a second bearing 64. In some embodiments, the first bearing 63 and the second bearing 64 are flanged bearings in which an extension or a lip on the outer ring of the bearing is designed to aid the mounting and positioning of the bearing. In some embodiments, a flange of the first bearing 63 is positioned on a surface of the base 61 facing towards the cover 62. In some embodiments, a flange of the second bearing 64 is positioned on a surface of the base 61 facing away from the cover 62.

In some embodiments, the adapter further includes a retaining ring 65. In some embodiments, the retaining ring 65 is radially installed on a groove 66-3 of the receiving shaft 66. The retaining ring 65 may be a C-ring. In some embodiments, a diameter of the receiving yoke 66-1 is greater than a diameter of the chuck 66-2. In this way, the receiving yoke 66-1 has a wider diameter than an inner ring of the bearings 63 and 64. The bearings 63 and 64 may be sandwiched between the receiving yoke 66-1 and the retaining ring 65. Thus, the receiving yoke 66-1 and the retaining ring 65 are used to aid the mounting and positioning of the receiving shaft 66.

Figure 7:
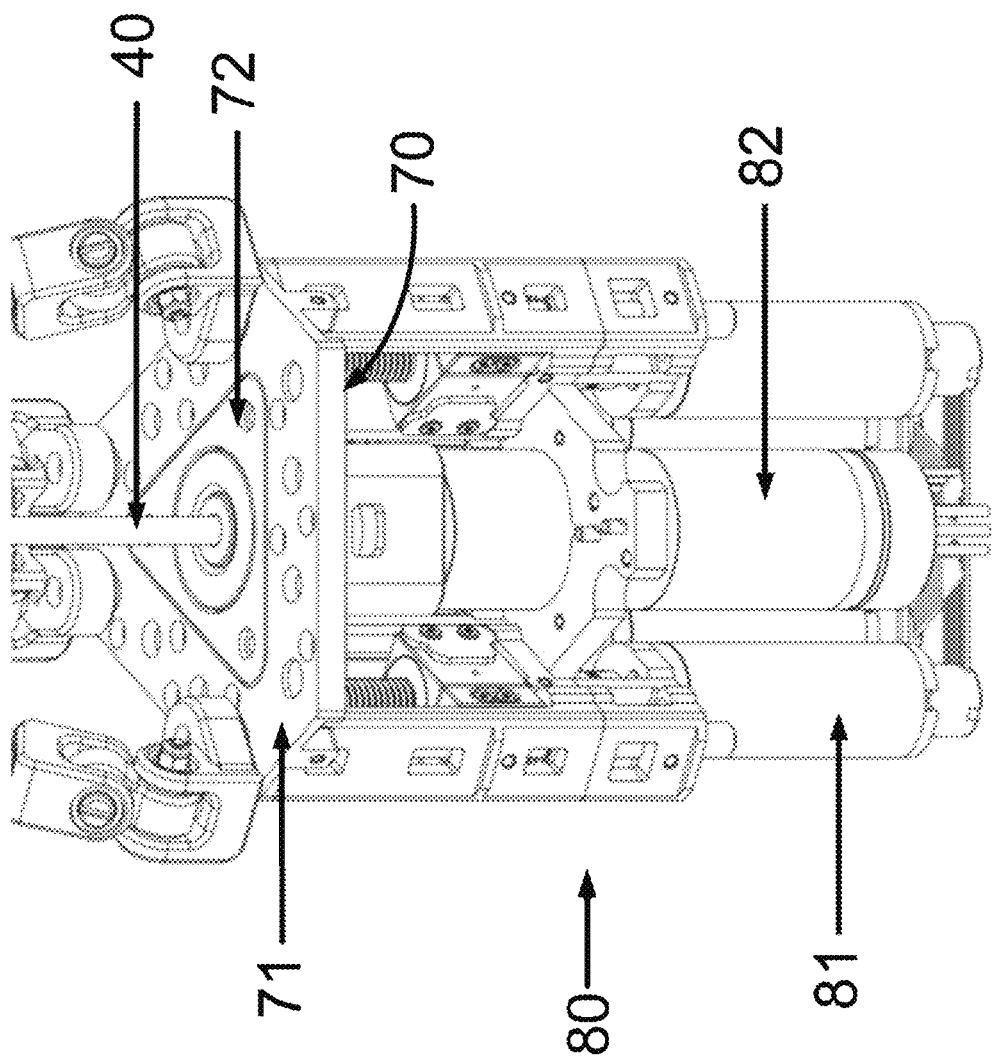
FIG. 7 illustrates a perspective view of a machine module according to some embodiments of the instant disclosure.

FIG. 7 illustrates an isometric view of a machine module according to some embodiments of the instant disclosure. In some embodiments, the machine module 80 is mechanically attached to a base platform 70 of a parallel manipulator. In some embodiments, machine module 80 includes a plurality of actuators 81 configured to control the movement of the plurality of limbs (i.e., limbs 11-3 in FIG. 1) of the parallel manipulator and a shaft motor 82 configured to generate a mechanical force for manipulating a surgical tool (i.e., surgical tool T1 in FIG. 1).

In some embodiments, as shown in FIG. 7, the base platform 70 includes a limb base 71 and a shaft base 72 surrounded by the limb base 71. The limb base 71 is used to provide structural support between the plurality of limbs of the parallel manipulator and the actuators 81 of the machine module 80. The shaft base 72 is used to provide structural support for the shaft motor 82. In some embodiments, a transmission shaft 40 is disposed within a recess area of the shaft base 72. A portion of the shaft motor 82 may be exposed in the recess area of the shaft base 72. The transmission shaft 40 and the shaft motor 82 may be slidingly engaged within the recess area of the shaft base 72.

Figure 8:
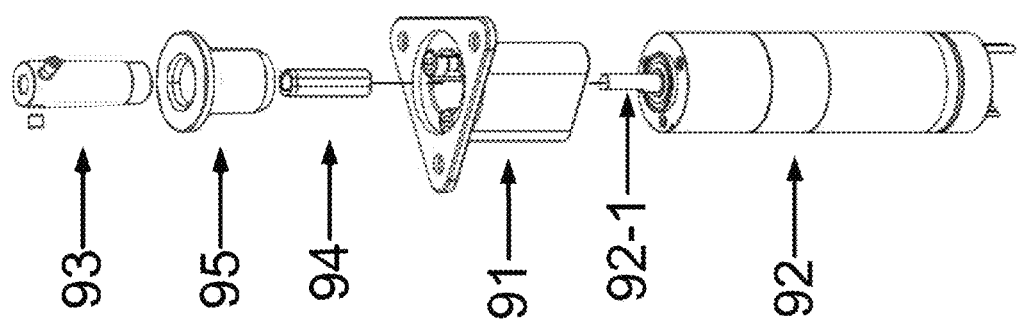
FIG. 8 illustrates an exploded view of a transmission shaft, a parallel manipulator, and a machine module according to some embodiments of the instant disclosure.

FIG. 8 illustrates an exploded view of a transmission shaft, a parallel manipulator, and a machine module according to some embodiments of the instant disclosure. A shaft motor 92 of the machine module is coupled the shaft base 91 of the parallel manipulator. In some embodiments, a rotor 92-1 of the shaft motor 92 is inserted into a recess area of the shaft base 91. A drive shaft 94 is attached to rotor 92-1 and configured to move in a same direction as the rotor 92-1. A runner 93 of a transmission shaft is slidingly engaged to the shaft motor 92. In some embodiments, the runner 93 is slidingly engaged to the drive shaft 94, in which the mechanical force generated by the shaft motor is transferred to the runner 93 through the drive shaft 94. The runner 93 has an inlet, and a cross-sectional profile of the drive shaft 94 is structurally complementary to a cross-sectional profile of the inlet. The inlet is configured to slide along the drive shaft 94. Further illustration and related explanation for the relation between the drive shaft and the runner shall be disclosed in FIG. 9.

In some embodiments, a barrel 95 is placed within a recess area of the shaft base 91. The barrel 95 surrounds the runner 93, while the runner 93 surrounds the drive shaft 94 when the medical device is assembled. The barrel 95, the runner 93, and the drive shaft 94 are successively fitted within each other.

In some embodiments, to reduce friction between the runner 93 and the drive shaft 94, a material of the runner 93 and the drive shaft 94 are different from each other. A Young's modulus of the drive shaft 94 is different from a Young's modulus of the runner 93. In some embodiments, a material of the runner 93 is steel, and a material of the drive shaft 94 is copper. In some embodiments, a material of the runner 93 and the drive shaft 94 are anti-friction metal-polymers.

In some embodiments, to reduce friction between the runner 93 and the drive shaft 94, a lubricant is coated on an outer surface of the drive shaft 94. In some embodiments, a lubricant is coated on an inner surface of the runner 93. The lubricant may include, at least one of, carbon powder, lubricating oil, etc.

In some embodiments, to reduce friction between the runner 93 and the barrel 95, a material of the runner 93 and the barrel 95 are different from each other. A Young's modulus of the runner 93 is different from a Young's modulus of the barrel 95. In some embodiments, a material of the runner 93 is steel and a material of the barrel 95 is copper. In some embodiments a material of the runner 93 and the barrel 95 are anti-friction metal-polymers.

In some embodiments, to reduce friction between the runner 93 and the barrel 95, a lubricant is coated on an outer surface of the runner 93. In some embodiments, a lubricant is coated on an inner surface of the barrel 95. The lubricant may include at least one of carbon powder, lubricating oil, etc.

Figure 9:
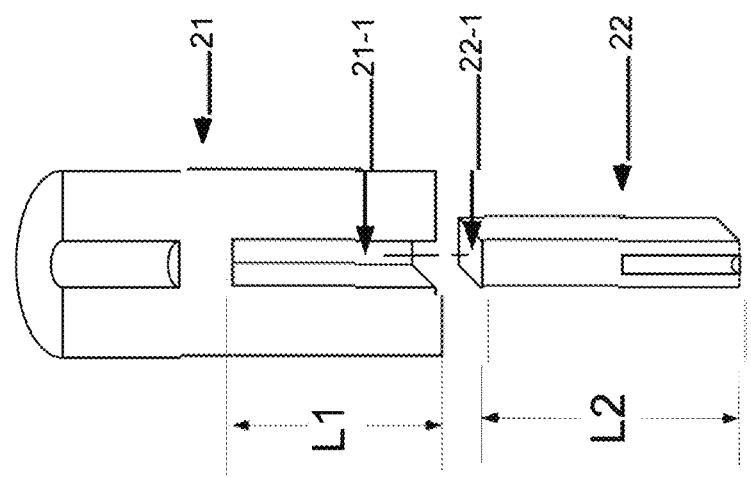
FIG. 9 illustrates a cross-sectional view of a drive shaft and a runner according to some embodiments of the instant disclosure.

FIG. 9 illustrates a cross-sectional view of a drive shaft and a runner according to some embodiments of the instant disclosure. A representative illustration of the runner 21 and the drive shaft 22 is provided to assist in description sliding engagement therebetween. The runner 21 has an inlet 21-1. A cross-sectional profile of a surface 22-1 of the drive shaft is structurally complementary to a cross-sectional profile of the inlet 21-1. The inlet 21-1 is configured to slide along the drive shaft 22 when necessary during operation of the medical device. In some other embodiments, an overlap between the drive shaft 22 and the runner 21 is needed during operation to ensure the transfer of mechanical force therebetween. The overlap between the drive shaft 22 and the runner 21 is no less than 5 mm during operation to ensure the transfer of mechanical force therebetween. In some other embodiments, a minimum overlap between the drive shaft 22 and the runner 21 is no more than 5 mm. In some other embodiments, a minimum overlap between the drive shaft 22 and the runner 21 ranges between 0 to 5 mm. In some further embodiments, a minimum overlap between the drive shaft 22 and the runner 21 ranges between 5 mm to 100 mm. In some embodiments, the depth L1 of the inlet 21-1 is greater than the height L2 of the drive shaft 22. In some other embodiments, the depth L1 of the inlet 21-1 is substantially the same as the height L2 of the drive shaft 22.

In some embodiments, the cross-sectional profiles of the inlet 21-1 and the surface 22-1 of the drive shaft 22 have a polygonal shape. The drive shaft 22 has a plurality of facets that meet each other to form angled intersections. In some embodiments, an intersection between two facets is rounded or curved to prevent damage during insertion. The inlet 21-1 is an enclosed-shaped opening that grips the facets of the drive shaft 22. The angle between facets of the drive shaft 22 provide grip to drive the runner 21.

In some other embodiments, the drive shaft and the runner have different structures used for transferring mechanical force. The drive shaft has a protrusion. The runner has a groove corresponding to the protrusion. In an assembled medical device, the protrusion of the drive shaft is inserted into the groove of the runner. The height of groove is enough to allow the protrusion to stay within the groove while the runner slides away from the drive shaft during operation. The protrusion is configured to slide along the corresponding groove. Further, the drive shaft is configured to transfer a mechanical force to the runner through a sidewall of the protrusion of drive shaft tangential to an inner sidewall of the groove of the runner when in motion.

In some embodiments, drive shaft has two protrusions extending in opposite direction from each other. The runner has two grooves complementary to the two protrusions of the drive shaft. In some embodiments, the drive shaft has a dogbone drive joint and the runner is a drive cup.

FIG. 10 illustrates a perspective view of a receiving shaft and a transmission yoke according to some embodiments of the instant disclosure. In some embodiments, a transmission yoke 102 of the transmission shaft has at least one protrusion 102-1. The at least one protrusion 102-1 extends from a body 102-2 of the transmission yoke 102. In some embodiments, the protrusion 102-1 is cylindrical in shape. The receiving shaft 101 has a receiving yoke 101-1. The receiving yoke 101-1 has grooves 101-2 structurally complementary to the at least one protrusion 102-1 of the transmission yoke 102. Upon assembly of the medical device, a top portion of the body 102-2 is inserted in a recessed area of the receiving yoke 101-1. During operation, the transmission yoke 102 is configured to transfer a mechanical force to the receiving yoke 101-1 through a sidewall of the protrusion 102-1 tangential to an inner sidewall of the groove 101-2. In this way, the contact between the receiving yoke 101-1 and the transmission yoke 102 is minimal during operation to prevent the transmission yoke 102 from generating unwanted noise.

In some embodiments, the transmission yoke 102 has two protrusions 102-1. The protrusions 102-1 extend from a sidewall of the transmission yoke 102 in opposite directions from each other. The two protrusions 102-1 are 180° apart from each other. The receiving yoke 101-1 has two grooves 101-2 complementary to the two protrusions 102-1. In the same way as the two protrusions 102-1, the two grooves 101-2 are disposed opposite of each other. In some embodiments, the transmission yoke 102 is a dogbone drive joint and the receiving yoke 101-1 is a drive cup.

Figure 11:
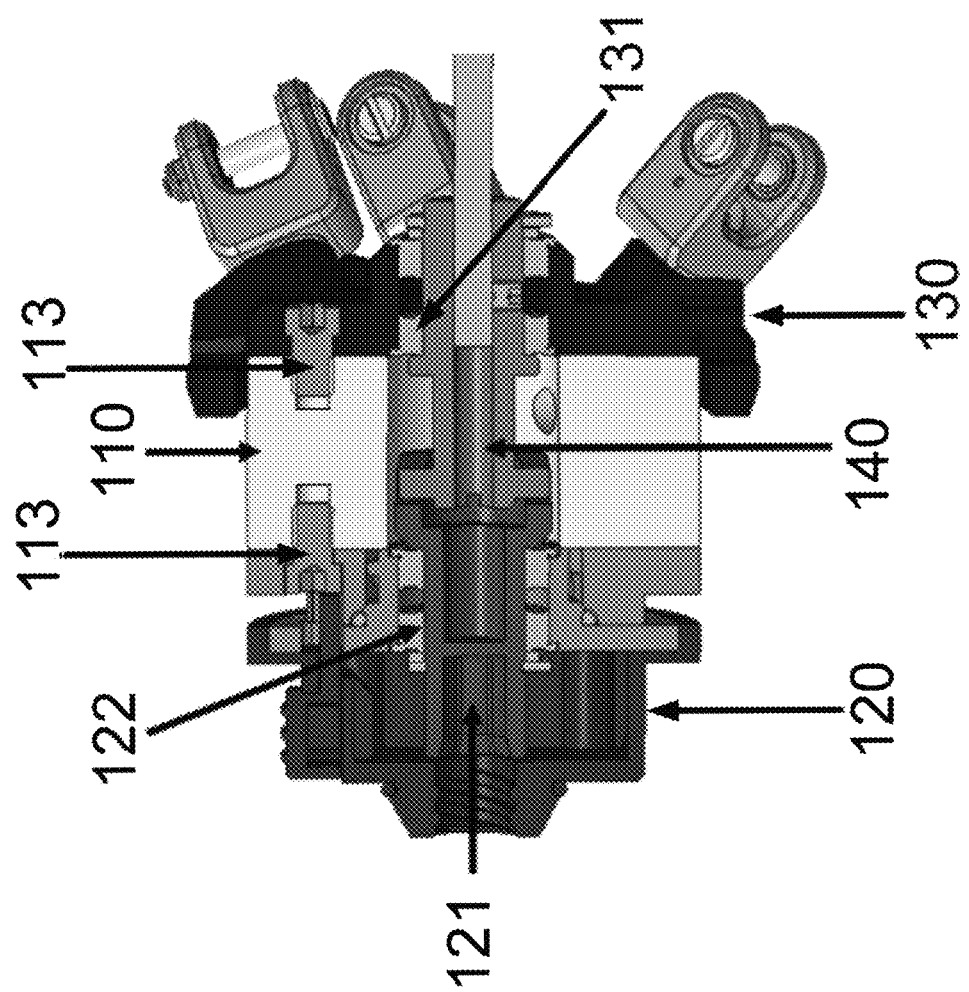
FIG. 11 illustrates a cross-sectional view of a force sensor according to some embodiments of the instant disclosure.
Figure 12:
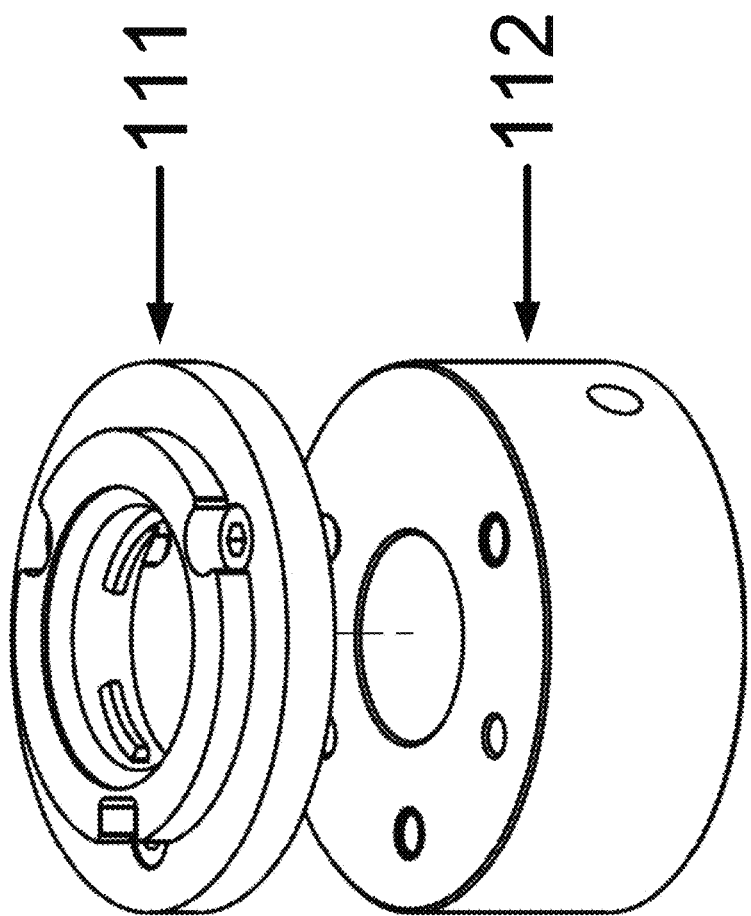
FIG. 12 illustrates an exploded view of a force sensor according to some embodiments of the instant disclosure.

During operation, the noise from the transmission shaft is minimized as much as possible so as to not cause problems when the motion of the surgical tool is monitored. In some embodiments, a sensor system can be used to monitor the surgical tool. FIG. 11 illustrates a cross-sectional view of a force sensor according to some embodiments of the instant disclosure. FIG. 12 illustrates an exploded view of a force sensor according to some embodiments of the instant disclosure. In some embodiments, the sensor system 110 is disposed between the end platform 130 and the adapter 120. The sensor system 110 is configured to measure force of the adapter 120. The sensor system 110 has a through hole where a receiving shaft 121 rotatably supported by a bearing 122 and a transmission shaft 140 rotatably supported by a bearing 131 meet.

In some embodiments, the sensor system 110 includes a force relay 111 and a force transducer 112 mechanically coupled to the force relay 111. The force relay 111 is detachably coupled to the adapter 120. In some embodiments, the force relay 111 has grooves and protrusion that interlocks with grooves and protrusion of the adapter 120.

In some embodiments, the force transducer 112 is mechanically attached to the force relay 111 and the end platform 130 and configured to convert a force applied to the adapter 120 into an electrical signal. In some embodiments, the force transducer 112 is mechanically attached to the force relay 111 and the end platform 130 using fasteners 113 embedded around the periphery of the through hole of the force transducer 112. In some embodiments, a plurality of holes are formed on the front surface and back surface of the force transducer 112 to correspondingly accommodate fasteners 113 for the force relay 111 and the end platform 130. In some embodiments, the fasteners 113 for the force relay 111 interposes with the fasteners 113 for the end platform 130. In some embodiments, the fasteners 113 for the force relay 111 are not aligned and do not have projections that overlap with projections of the fasteners 113 for the end platform 130.

In some embodiments, the force transducer 112 is a donut load cell (also known as a load washer or thru-hole load cell). The force transducer 112 converts a force such as tension, compression, pressure, or torque into an electrical signal. In some embodiments, the force applied to the force transducer 112 is proportional to the change in the electrical signal.

In some embodiments, the applied force to the adapter 120, aside from predetermined force and predetermined torque, further includes a force deviation and a torque deviation that is measured during operation. The force deviation indicates the influence in the direction of the receiving shaft when the surgical tool disposed on the receiving shaft 121 comes in contact with and exerts force on a target object, such as bone, during operation. The torque deviation indicates the influence in the motion of the receiving shaft when the surgical tool disposed on receiving shaft 121 comes in contact with and exerts force on target object, such as bone, during operation.

In some embodiments, the sensor system 110 is used in controlling the position and orientation of the surgical tool during operation. In some embodiments, the sensor system is signally connected to a controller. During operation, an operation plan with predetermined range, the predetermined path, or the combination thereof is received by the controller. The sensor system measures the force deviation, the torque deviation, or the combination thereof. The force deviation and the torque deviation are deviations from the predetermined range (i.e., predetermined force and predetermined torque) of the operation plan. The orientation and position of the surgical tool is adjusted based on the force deviation and the torque deviation. The orientation and position of the surgical tool is adjusted by controlling the actuators that move the parallel manipulator. The movement of the surgical tool is adjusted by controlling the mechanical force from the shaft motor. In some embodiments, the transmission shaft may cause noise on the sensor system. Thus, in some embodiments, a low pass filter is further electrically coupled to the sensor system to remove noise.

Therefore, one aspect of the instant disclosure provides a medical device that includes a parallel manipulator, an adapter, a transmission shaft and a shaft motor. The parallel manipulator includes an end platform and a base platform mechanically coupled to the end platform. The adapter includes a body detachably coupled to the end platform and a receiving shaft rotatably supported by the body, and the receiving shaft having a receiving yoke. The transmission shaft is rotatably supported by the end platform, and the transmission shaft includes a transmission yoke configured to transfer mechanical force to the receiving yoke, a first rod coupled to the transmission yoke, a second rod coupled to the first rod, a universal joint coupled between the first rod and the second rod, and a runner coupled to the second rod. The shaft motor is configured to generate mechanical force to drive the transmission shaft, and the shaft motor has a drive shaft slidably engaged to the runner.

In some embodiments, the medical device further comprises a sensor system disposed between the end platform and the adapter, the sensor system is configured to measure force on the adapter.

In some embodiments, the sensor system comprises a force relay detachably coupled to the adapter; and a force transducer mechanically attached to the force relay and the end platform, and configured to convert a force applied to the adapter into an electrical signal.

In some embodiments, the transmission yoke has a protrusion and the receiving yoke has a groove structurally complementing the protrusion. In some embodiments, the transmission yoke is configured to transfer the mechanical force to the receiving yoke through a sidewall of the protrusion, the sidewall being tangential to the groove.

In some embodiments, the runner has an inlet. A cross-sectional profile of the drive shaft is structurally complementary to a cross-sectional profile of the inlet. The inlet is configured to slide along the drive shaft.

In some embodiments, the cross-sectional profiles of the inlet and the drive shaft have a polygonal shape.

In some embodiments, the drive shaft has a protrusion and the runner has a groove corresponding to the protrusion. In some embodiments, the protrusion is configured to slide along the groove.

In some embodiments, a minimum overlap between the drive shaft and the runner is no less than 5 mm.

In one embodiment, the universal joint includes a first coupler coupled to the first rod, a second coupler coupled to the first coupler, and a third coupler coupled between the second coupler and the second rod. The first coupler is pivotably coupled with the second coupler through a first connecting shaft and a second connecting shaft, and the first coupler is swingable with respect to the second coupler along a first direction and a second direction. The second coupler is pivotably coupled with the third coupler through a third connecting shaft and a fourth connecting shaft, and the second coupler is swingable with respect to the third coupler along the first direction and the second direction.

In some embodiments, the universal joint further includes a fourth coupler coupled to the first coupler and the second coupler, and a fifth coupler coupled between the second coupler and the third coupler. The first coupler is pivotably coupled to the fourth coupler rotatably about the first connecting shaft, and the second coupler is pivotably coupled to the fourth coupler rotatably about the second connecting shaft. The second coupler is pivotably coupled to the fifth coupler rotatably about the third connecting shaft, and the third coupler is pivotably coupled to the fifth coupler rotatably about the fourth connecting shaft.

In some embodiments, the medical device further comprises a barrel surrounding the runner. The barrel, the runner, and the drive shaft are successively fitted within one another.

In some embodiments, a Young's modulus of the drive shaft is different from a Young's modulus of the runner, and the Young's modulus of the runner is different from a Young's modulus of the barrel.

In some embodiments, the medical device further includes a lubricant that is coated on a surface of at least one of the barrel, the runner, and the drive shaft.

In some embodiments, when the end platform and the base platform have a minimum distance therebetween, the universal joint is in normal state.

In some embodiments, the force transducer is a donut load cell.

In some embodiments, the adapter further has a bearing configured to rotatably attach the receiving shaft to the body. In some embodiments, the end platform further has a bearing configured to rotatably attach the transmission shaft to the end platform.

Those skilled in the art will readily observe that numerous modifications and alterations of the device and method may be made while retaining the teachings of the present disclosure. Accordingly, the above disclosure should be construed as being limited only by the metes and bounds of the appended claims.

What is claimed is:

1. A medical device, comprising:
   a parallel manipulator, an adapter, a transmission shaft and a shaft motor, wherein the parallel manipulator includes:
   an end platform; and
   a base platform mechanically coupled to the end platform;
   wherein the adapter includes:
   a body detachably coupled to the end platform; and
   a receiving shaft rotatably supported by the body, and the receiving shaft having a receiving yoke;
   wherein the transmission shaft is rotatably supported by the end platform, and the transmission shaft includes:
   a transmission yoke configured to transfer mechanical force to the receiving yoke;
   a first rod coupled to the transmission yoke;
   a second rod coupled to the first rod;
   a universal joint coupled between the first rod and the second rod; and
   a runner coupled to the second rod; and
   wherein the shaft motor is configured to generate mechanical force to drive the transmission shaft, and the shaft motor has a drive shaft slidably engaged to the runner.

2. The medical device according to claim 1, wherein the transmission yoke has a protrusion and the receiving yoke has a groove structurally complementary to the protrusion; and
   wherein the transmission yoke is configured to transfer the mechanical force to the receiving yoke through a sidewall of the protrusion, the sidewall being tangential to the groove.

3. The medical device according to claim 1, wherein the drive shaft has a protrusion, the runner has a groove corresponding to the protrusion, and the protrusion is configured to slide along the corresponding groove.

4. The medical device according to claim 1, wherein a minimum overlap between the drive shaft and the runner is no less than 5 mm.

5. The medical device according to claim 1, wherein, when the end platform and the base platform have a minimum distance therebetween, the universal joint is in a normal state.

6. The medical device according to claim 1, wherein the adapter further has a first bearing configured to rotatably attach the receiving shaft to the body; and
   wherein the end platform further has a second bearing configured to rotatably attach the transmission shaft to the end platform.

7. The medical device according to claim 1, wherein the runner has an inlet, and a cross-sectional profile of the drive shaft is structurally complementary to a cross-sectional profile of the inlet; and
   wherein the inlet is configured to slide along the drive shaft.

8. The medical device according to claim 7, wherein the cross-sectional profiles of the inlet and the drive shaft have a polygonal shape.

9. The medical device according to claim 1, wherein the universal joint includes:
   a first coupler coupled to the first rod;
   a second coupler coupled to the first coupler; and a third coupler coupled between the second coupler and the second rod;

wherein the first coupler is pivotably coupled with the second coupler through a first connecting shaft and a second connecting shaft, and the first coupler is swingable with respect to the second coupler along a first direction and a second direction; and wherein the second coupler is pivotably coupled with the third coupler through a third connecting shaft and a fourth connecting shaft, and the second coupler is swingable with respect to the third coupler along the first direction and the second direction.

10. The medical device according to claim 9, wherein the universal joint further includes:

a fourth coupler coupled to the first coupler and the second coupler, the first coupler is pivotably coupled to the fourth coupler rotatably about the first connecting shaft, and the second coupler is pivotably coupled to the fourth coupler rotatably about the second connecting shaft; and a fifth coupler coupled between the second coupler and the third coupler, the second coupler is pivotably coupled to the fifth coupler rotatably about the third connecting shaft, and the third coupler is pivotably coupled to the fifth coupler rotatably about the fourth connecting shaft.

11. The medical device according to claim 1, further comprising:

a barrel surrounding the runner, wherein the barrel, the runner, and the drive shaft are successively fitted within one another.

12. The medical device according to claim 11, wherein a Young's modulus of the drive shaft is different from a Young's modulus of the runner, and the Young's modulus of the runner is different from a Young's modulus of the barrel.

13. The medical device according to claim 11, wherein the medical device further includes a lubricant that is coated on a surface of at least one of the barrel, the runner, and the drive shaft.

14. The medical device according to claim 1, further comprising:

a sensor system disposed between the end platform and the adapter, wherein the sensor system is configured to measure force on the adapter.

15. The medical device according to claim 14, wherein the sensor system includes:

a force relay detachably coupled to the adapter; and a force transducer mechanically attached to the force relay and the end platform, wherein the force transducer is configured to convert a force applied to the adapter into an electrical signal.

16. The medical device according to claim 15, wherein the force transducer is a donut load cell.

* * * * *